(12) United States Patent
Morita et al.

(10) Patent No.: US 9,846,216 B2
(45) Date of Patent: Dec. 19, 2017

(54) MAGNETIC RESONANCE IMAGING APPARATUS AND MAGNETIC RESONANCE IMAGING METHOD

(71) Applicant: TOSHIBA MEDICAL SYSTEMS CORPORATION, Otawara-shi, Tochigi (JP)

(72) Inventors: Yoshinari Morita, Tochigi (JP); Hiroshi Takai, Tochigi (JP); Yoshiteru Watanabe, Tochigi (JP); Takashi Shigeta, Tochigi (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 341 days.

(21) Appl. No.: 14/865,509

(22) Filed: Sep. 25, 2015

(65) Prior Publication Data
US 2016/0018500 A1 Jan. 21, 2016

Related U.S. Application Data

(63) Continuation of application No. PCT/JP2014/058340, filed on Mar. 25, 2014.

(30) Foreign Application Priority Data

Mar. 26, 2013 (JP) .................. 2013-065260

(51) Int. Cl.
*G01V 3/00* (2006.01)
*G06K 9/00* (2006.01)
(Continued)

(52) U.S. Cl.
CPC .......... *G01R 33/5616* (2013.01); *A61B 5/055* (2013.01); *A61B 5/7203* (2013.01);
(Continued)

(58) Field of Classification Search
CPC .......... G01R 33/5616; G01R 33/34046; G01R 33/385; G01R 33/56554; G01R 33/5617; A61B 5/7203; A61B 5/055
(Continued)

(56) References Cited

U.S. PATENT DOCUMENTS 8,126,237 B2  2/2012 Kimura
2009/0010514 A1* 1/2009 Kimura ............ G01R 33/56509
382/131

FOREIGN PATENT DOCUMENTS

JP  9-253069     9/1997
JP  2001-292976  10/2001
WO  WO 2006/051911 5/2006

OTHER PUBLICATIONS

Notification of Transmittal of Translation of the International Preliminary Report on Patentability in PCT/JP2014/058340 dated Oct. 8, 2015.
(Continued)

*Primary Examiner* — Farhana Hoque
(74) *Attorney, Agent, or Firm* — Nixon & Vanderhye P.C.

(57) ABSTRACT

According to one embodiment, an MRI apparatus includes a data acquiring unit and processing circuitry. The data acquiring unit acquires MR signals for imaging according to data acquiring conditions for acquiring MR signals multiple times following one excitation. The data acquiring unit also acquires reference MR signals for phase correction of real space data for imaging. The real space data are generated based on the MR signals for imaging. The processing circuitry is configured to calculate a phase error, in a real space region, of reference real space data and generate MR image data based on the MR signals for imaging with the phase correction of the real space data for imaging based on the calculated phase error. The reference real space data are generated based on the reference MR signals. The real space
(Continued)

region is determined based on conditions of acquiring the reference MR signals or the like.

16 Claims, 13 Drawing Sheets

(51) Int. Cl.
    *G01R 33/561*     (2006.01)
    *A61B 5/055*     (2006.01)
    *G01R 33/565*     (2006.01)
    *A61B 5/00*     (2006.01)
    *G01R 33/34*     (2006.01)
    *G01R 33/385*     (2006.01)

(52) U.S. Cl.
    CPC ..... *G01R 33/34046* (2013.01); *G01R 33/385* (2013.01); *G01R 33/5617* (2013.01); *G01R 33/56554* (2013.01)

(58) Field of Classification Search
    USPC .................................. 324/306–309; 382/131
    See application file for complete search history.

(56) References Cited

OTHER PUBLICATIONS

First JP Office Action dated Aug. 9, 2016 in Japanese Patent Application No. JP 2013-065260.
International Search Report for PCT/JP2014/058340, dated Jun. 10, 2014, 2 pages.
Written Opinion of the ISA for PCT/JP2014/058340, dated Jun. 10, 2014, 4 pages.
Ahn et al., "A New Phase Correction Method in NMR Imaging Based on Autocorrelation and Histogram Analysis", IEEE Transactions on Medical Imaging, vol. MI-6, No. 1, pp. 32-36, Mar. 1987.

* cited by examiner

MAGNETIC RESONANCE IMAGING APPARATUS AND MAGNETIC RESONANCE IMAGING METHOD

CROSS REFERENCES TO RELATED APPLICATIONS

This is a continuation of Application PCT/JP2014/58340, filed on Mar. 25, 2014.

This application is based upon and claims the benefit of priority from Japanese Patent Application No. 2013-065260 filed on Mar. 26, 2013; the entire contents of which are incorporated herein by reference.

FIELD

Embodiments described herein relate generally to an MRI (magnetic resonance imaging) apparatus and a magnetic resonance imaging method.

BACKGROUND

The MRI apparatus is an imaging diagnostic apparatus which magnetically excites nuclear spins of an object set in a static magnetic field with RF (radio frequency) signals having the Larmor frequency and reconstructs an image based on MR (magnetic resonance) signals generated due to the excitation.

As a high speed imaging method in an MRI apparatus, an imaging method, such as an FSE (fast spin echo) method or an EPI (echo planar imaging) method, which acquires MR echo signals by one excitation is known. In such an imaging method which performs a multi-echo acquisition, MR signals are sequentially acquired by continuously repeating an application of a 180 degree RF pulse or an inversion of a gradient magnetic field for readout.

However, there is a problem that phases of MR signals do not align due to factors, such as non-uniformity in a magnetic field. Thus, phase errors of image signals are estimated, and a phase correction of the image signals is performed based on the estimated phase errors, in a high speed imaging method, such as the FSE method or the EPI method.

PRIOR TECHNICAL LITERATURE

[Patent literature 1] JPA H09-253069
[Nonpatent literature 1] "A New Phase Correction Method in NMR Imaging Based on Autocorrelation and Histogram Analysis", IEEE TRANSACTIONS ON MEDICAL IMAGING, VOL. MI-6, NO. 1, March 1987

An object of the present invention is to provide a magnetic resonance imaging apparatus and a magnetic resonance imaging method which can perform a more appropriate phase correction of MR signals in an imaging method, such as the FSE method or the EPI method, which acquires MR signals by one excitation.

BRIEF DESCRIPTION OF THE DRAWINGS

In the accompanying drawings.

DETAILED DESCRIPTION

In general, according to one embodiment, a magnetic resonance imaging apparatus includes a magnet, a gradient coil, at least one radio frequency coil and processing circuitry. The magnet, the gradient coil and the at least one radio frequency coil acquires magnetic resonance signals for imaging according to data acquiring conditions for acquiring magnetic resonance signals multiple times following one excitation. The magnet, the gradient coil and the at least one radio frequency coil also acquires magnetic resonance signals for reference for a phase correction of real space data for the imaging. The real space data are generated based on the magnetic resonance signals for the imaging. The processing circuitry is configured to calculate a phase error, in a real space region, of real space data for reference and generate magnetic resonance image data based on the magnetic resonance signals for the imaging with the phase correction of the real space data for the imaging based on the calculated phase error. The real space data for the reference are generated based on the magnetic resonance signals for the reference. The real space region is determined based on conditions of acquiring the magnetic resonance signals for the reference or conditions corresponding to the conditions of acquiring the magnetic resonance signals for the reference.

In addition, according to one embodiment, a magnetic resonance imaging method includes: acquiring magnetic resonance signals for imaging according to data acquiring conditions for acquiring magnetic resonance signals multiple times following one excitation, and acquiring magnetic resonance signals for reference for a phase correction of real space data for the imaging; and calculating a phase error, in a real space region, of real space data for reference and generating magnetic resonance image data based on the magnetic resonance signals for the imaging with the phase correction of the real space data for the imaging based on the calculated phase error. The real space data for the imaging are generated based on the magnetic resonance signals for the imaging. The real space data for the reference are generated based on the magnetic resonance signals for the reference. The real space region is determined based on conditions of acquiring the magnetic resonance signals for the reference or conditions corresponding to the conditions of acquiring the magnetic resonance signals for the reference.

A magnetic resonance imaging apparatus and a magnetic resonance imaging method according to embodiments of the present invention will be described with reference to the accompanying drawings.

Figure 1:
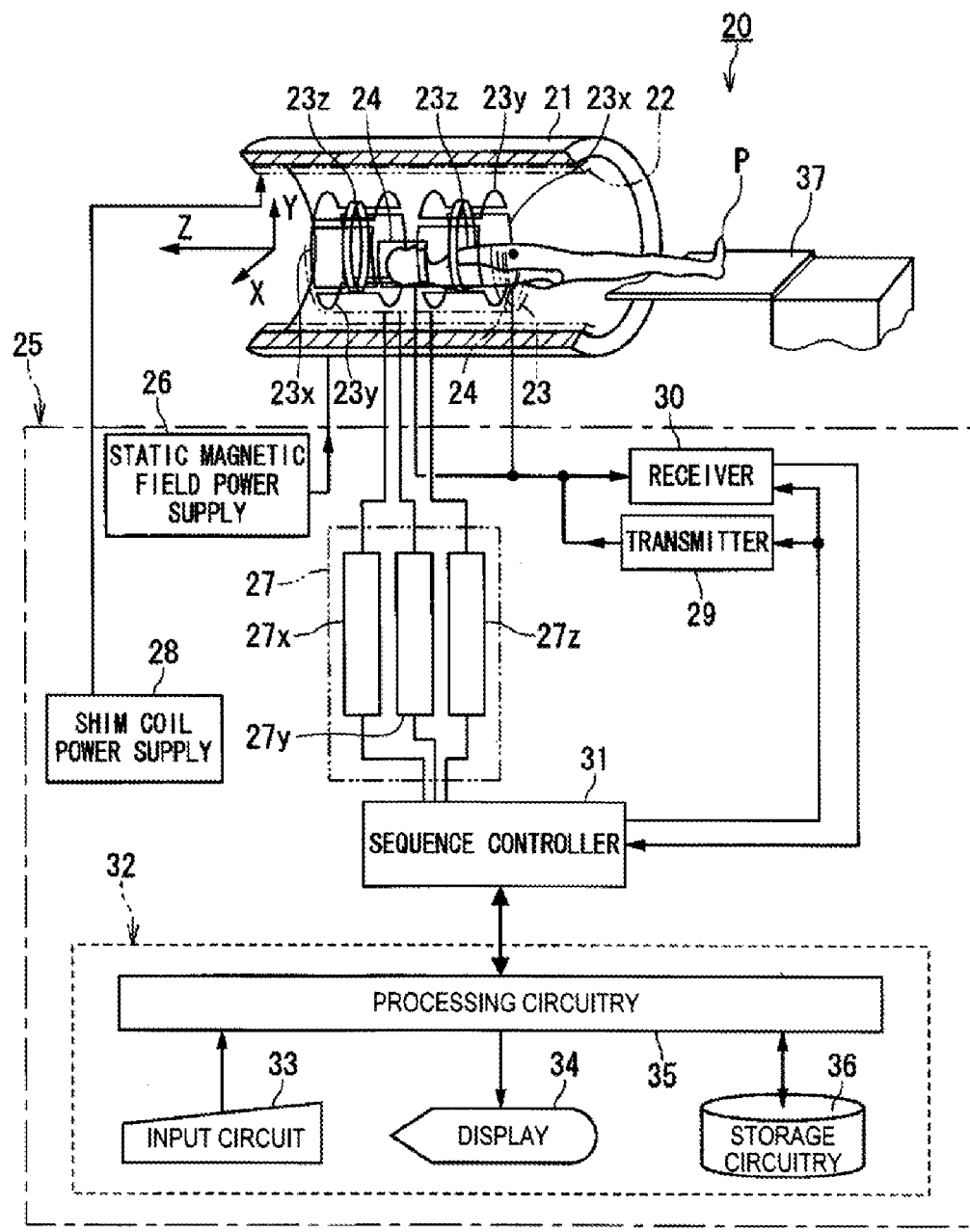
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a cylinder-shaped static field magnet 21, a shim coil 22, a gradient coil 23 and RF coils 24. The static field magnet 21 generates a static magnetic field. The shim coil 22 is arranged inside the static field magnet 21.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input circuit 33, a display 34, processing circuitry 35 and storage circuitry 36.

The static field magnet 21 communicates with the static magnetic field power supply 26. The static magnetic field power supply 26 supplies electric current to the static field magnet 21 to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z, which is cylinder-shaped, is arranged inside the static field magnet 21. The gradient coil 23 has also a bed 37 in the area formed inside it which is an imaging area. The bed 37 supports an object P. The RF coils 24 include a WBC (whole body coil), which is built in a gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 transmits RF signals given from the transmitter 29 to the object P. The reception RF coil 24 receives MR signals generated due to nuclear spins inside the object P which are excited by the RF signals to give to the receiver 30.

Figure 2:
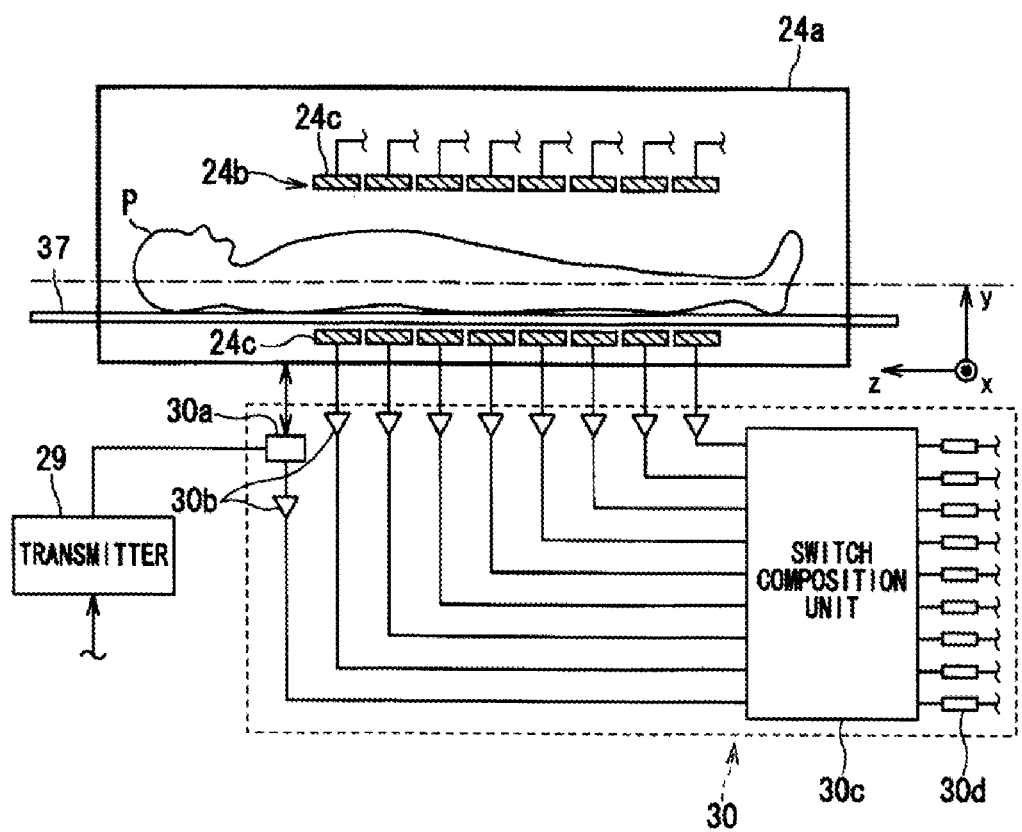
FIG. 2 is a diagram showing an example of detail structure of the RF coils shown in FIG. 1.
Figure 3:
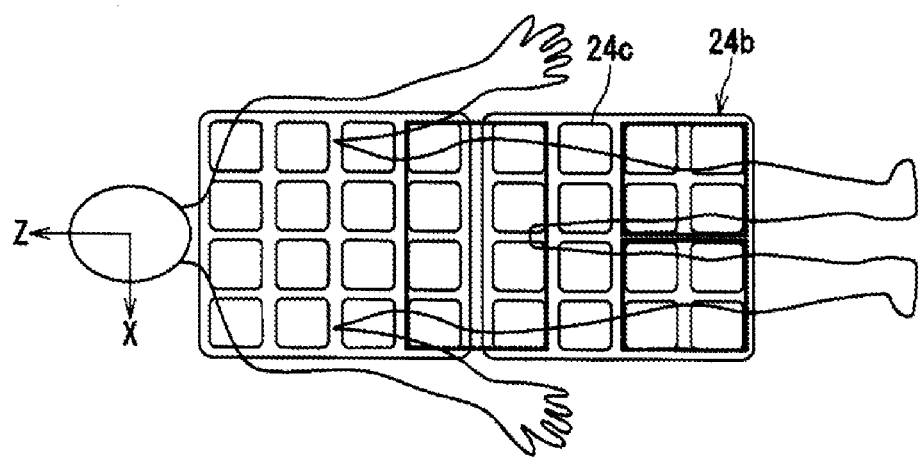
FIG. 3 is a diagram showing an example arrangement of the coil elements set on the body surface side of the object shown in FIG. 2.
Figure 4:
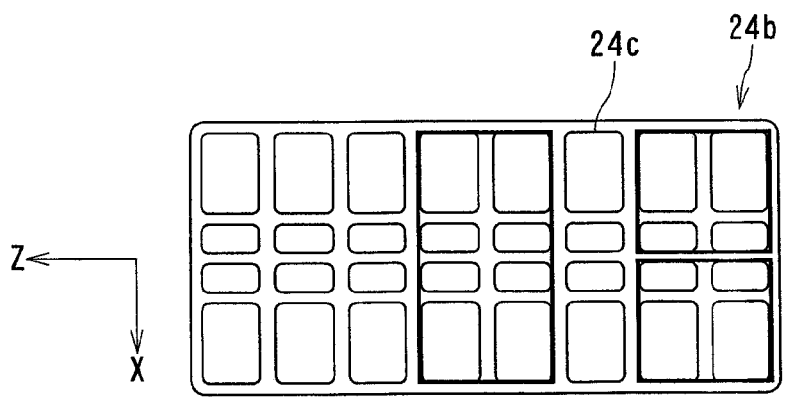
FIG. 4 is a diagram showing an example arrangement of the coil elements set on the back surface side of the object shown in FIG. 2.

FIG. 2 is a diagram showing an example of detail structure of the RF coils 24 shown in FIG. 1. FIG. 3 is a diagram showing an example arrangement of the coil elements 24c set on the body surface side of the object P shown in FIG. 2. FIG. 4 is a diagram showing an example arrangement of the coil elements 24c set on the back surface side of the object P shown in FIG. 2.

As shown in FIG. 2, the RF coils 24 include a cylindrical WB (whole-body) coil 24a, and a phased array coil 24b. The phased array coil 24b includes a plurality of coil elements 24c, and a plurality of the coil elements 24c is arranged on each of the body surface side and the back surface side of the object P.

For example, as shown in FIG. 3, on the body surface side of the object P, four rows of coil elements 24c are provided in the x-direction and eight columns of them in the z-direction, that is, a total of thirty two coil elements 24c are arranged so as to cover a wide-ranging imaging area. Likewise, as shown in FIG. 4, on the back surface side of the object, four rows of coil elements 24c are provided in the x-direction and eight columns of them in the z-direction, that is, a total of thirty two coil elements 24c are arranged so as to cover a wide-ranging imaging area. On the back surface side, coil elements 24 with a smaller size than that of the other coil elements 24c are arranged in the vicinity of the body axis from the viewpoint of sensitivity improvement, considering for the presence of the backbone of the object P.

On the other hand, the receiver 30 includes a duplexer 30a, amplifiers 30b, a switch composition unit 30c, and reception circuits 30d. The duplexer 30a is connected to the transmitter 29, the WB coil 24a, and the amplifier 30b for the WB coil 24a. The amplifiers 30b are provided by the total number of the coil elements 24c and the WB coil 24a, and each connected to a respective one of the coil elements 24c and the WB coil 24a. The switch composition unit 30c consists of a single piece or a plurality of pieces. The input side of the switch composition unit 30c is connected to the plurality of coil element units 24c or the WB coil 24a through the plurality of amplifiers 30b. The reception circuits 30d are provided by a desired number such as to be smaller than or equal to the total number of the coil elements 24c and the WB coil 24a, and disposed on the output side of the switch composition unit 30c.

The WB coil 24a can be used as a coil for the transmission of RF signals. As a coil for the reception of MR signals, each of the coil elements 24c can be used. Furthermore, the WB coil 24a can also be used for a receiving coil.

Therefore, the duplexer 30a is configured so as to provide the WB coil 24a with RF signals for transmission, output from the transmitter 29, while providing the switch composition unit 30c with MR signals received in the WB coil 24a via the amplifiers 30*b* in the receiver 30. An MR signal received in each of the coil elements 24*c* is output to the switch composition unit 30*c* via a respective one of the amplifiers 30*b*.

The switch composition unit 30*c* is configured so as to perform composition processing and switching with respect to MR signals received from the coil elements 24*c* or the WB coil 24*a* and to output them to the corresponding reception circuits 30*d*. In other words, the switch composition unit 30*c* is configured so that, in conformance with the number of the reception circuits 30*d*, the composition processing and switching with respect to MR signals received from the coil elements 24*c* or the WB coil 24*a* are performed in the switch composition unit 30*c*, and that MR signals can be received from various imaging areas by forming sensibility distributions in response to the imaging areas, using a plurality of desired coil elements 24*c*.

However, MR signals may be received by WB coil 24*a* alone without providing the coil elements 24*c*. Also, MR signals received in the coil elements 24*c* or the WB coil 24*a* may be directly output to the reception circuits 30*d* without providing the switch composition unit 30*c*. Furthermore, more coil elements 24*c* may be extensively arranged.

The sequence controller 31 of the control system 25 communicates with the gradient power supply 27, the transmitter 29 and the receiver 30. The sequence controller 31 stores sequence information describing control information needed in order to drive the gradient power supply 27, the transmitter 29 and the receiver 30, and generates gradient magnetic fields Gx, Gy and Gz in the X, Y and Z directions and RF signals by driving the gradient power supply 27, the transmitter 29 and the receiver 30 according to a predetermined stored sequence. The above-described control information includes motion control information, such as intensities, application durations and application timings of electric current pulses which should be applied to the gradient power supply 27.

The sequence controller 31 is also configured to give raw data to the computer 32. The raw data, which are complex-valued data, are generated by the receiver 30 performing detection and A/D (analog to digital) conversion of MR signals.

The transmitter 29 gives RF signals to the RF coil 24 in accordance with control information provided from the sequence controller 31. Meanwhile, the receiver 30 performs detection, necessary signal processing and A/D conversion of MR signals given from the RF coils 24 to generate raw data which are digitized complex-valued data. The generated raw data are given from the receiver 30 to the sequence controller 31.

The computer 32 has various functions by the processing circuitry 35 executing programs stored in the storage circuitry 36 of the computer 32. Alternatively, programs be stored in the processing circuitry 35.

Figure 5:
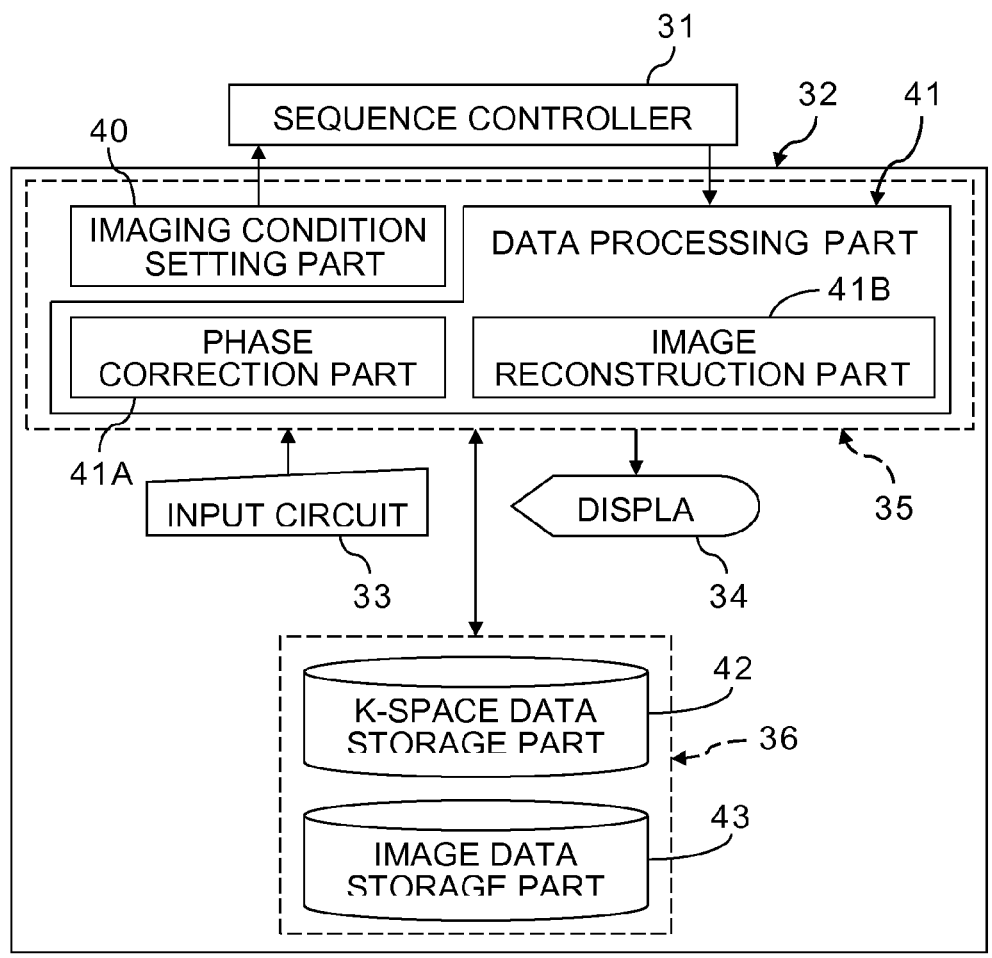
FIG. 5 is a functional block diagram of the computer shown in FIG. 1.

FIG. 5 is a functional block diagram of the computer 32 shown in FIG. 1.

The processing circuitry 35 of the computer 32 functions as an imaging condition setting part 40 and a data processing part 41 by executing programs stored in the storage circuitry 36. The data processing part 41 has a phase correction part 41A and an image reconstruction part 41B. Moreover, the storage circuitry 36 functions as a k-space data storage part 42 and an image data storage part 43.

The imaging condition setting part 40 has a function to set imaging conditions including a pulse sequence based on direction information from a input circuit 33 and output the set imaging conditions to the sequence controller 31. In particular, the imaging condition setting part 40 can set a pulse sequence, such as an FSE sequence or an EPI sequence, which acquires MR echo signals by one excitation, as imaging conditions.

Figure 6:
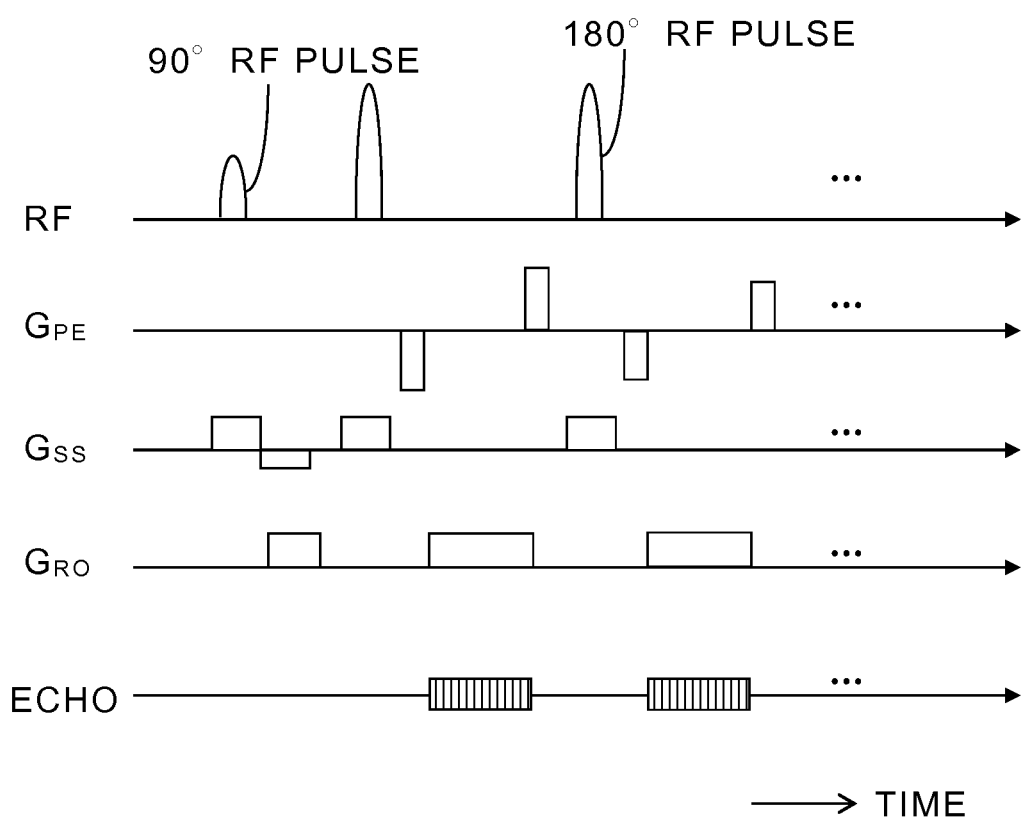
FIG. 6 shows an example of FSE sequence which can be set in the imaging condition setting part shown in FIG. 5.

FIG. 6 shows an example of FSE sequence which can be set in the imaging condition setting part 40 shown in FIG. 5.

In FIG. 6, each horizontal axis shows time, RF shows RF transmission pulses, $G_{SS}$ shows SS (slice selection) gradient magnetic field pulses, $G_{PE}$ shows PE (phase encode) gradient magnetic field pulses, $G_{RO}$ shows RO (readout) gradient magnetic field pulses, and ECHO shows MR echo signals, respectively.

As shown in FIG. 6, the FSE sequence applies a 90° RF pulse together with an SS gradient magnetic field pulse to excite a selected slice, and subsequently repeatedly applies a 180° RF pulse together with an SS gradient magnetic field pulse in order to continuously acquire MR echo signals. In the FSE sequence, the intensity of an PE gradient magnetic field pulse applied before each of RO gradient magnetic field pulses for acquiring MR echo signals is set so as to change gradually, in order to acquire MR echo signals necessary for imaging. That is, the MR echo signals are acquired with changing a PE amount.

Figure 7:
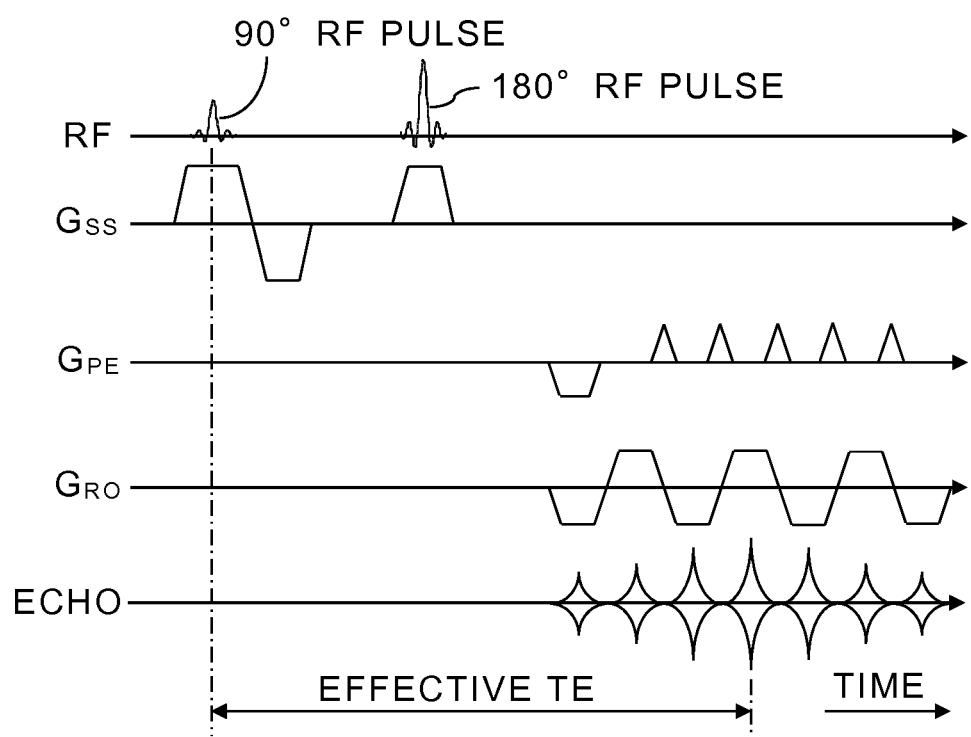
FIG. 7 shows an example of EPI sequence which can be set in the imaging condition setting part shown in FIG. 5.

FIG. 7 shows an example of EPI sequence which can be set in the imaging condition setting part 40 shown in FIG. 5.

In FIG. 7, each horizontal axis shows time, RF shows RF transmission pulses, $G_{SS}$ shows SS gradient magnetic field pulses, $G_{PE}$ shows PE gradient magnetic field pulses, $G_{RO}$ shows RO gradient magnetic field pulses, and ECHO shows MR echo signals, respectively.

As shown in FIG. 7, the EPI sequence applies a 90° RF pulse and a 180° RF pulse to excite a slice selected by applying SS gradient magnetic field pulses, and subsequently repeatedly applies a PE gradient magnetic field pulse and an RO gradient magnetic field pulse in order to continuously acquire MR echo signals from the selected slice. The period from the application time of the 90° RF pulse to the acquisition time of echo signals at the center of k-space is called effective TE (echo time).

A sequence repeating a multi-echo acquisition sequence, which continuously acquires MR signals as shown in FIG. 6 or FIG. 7, may also be set. A sequence, which acquires all MR signals necessary for generating MR image data by one excitation by applying a 90° RF pulse, is called a single shot multi-echo sequence. Meanwhile, a sequence, which acquires all MR signals necessary for generating MR image data by plural excitations by applying a 90° RF pulse multiple times, is called a multi-shot multi-echo sequence.

When MR signals are acquired by a single shot multi-echo sequence or a multi-shot multi-echo sequence, phase errors arise in real space data generated based on the MR signals because of factors, such as non-uniformity in a magnetic field. Therefore, phase correction processing of the real space data becomes essential in order to generate MR image data without an influence of the phase errors.

In the phase correction processing, a 1D (one dimensional) MR signal train, desirably acquired with setting a PE amount to zero, is referred to as reference MR data. As a matter of course, it is also possible to acquire the reference MR data without setting the PE amount to zero. Hereinafter, a case where the reference MR data are acquired with setting the PE amount to zero will be described. The reference MR data acquired with setting the PE amount to zero are MR data without phase errors by a PE gradient magnetic field. Therefore, phase errors of real space data which are mainly due to non-uniformity in a magnetic field can be estimated with high accuracy, based on the reference MR data.

Accordingly, the imaging condition setting part 40 sets conditions for acquiring reference MR data besides conditions for acquiring MR signals as imaging data. A sequence for acquiring the reference MR data is a sequence in which PE gradient magnetic field pulses are not applied in the multi-echo acquisition sequence shown in FIG. 6 or FIG. 7.

Thus, MR signals for imaging can be acquired according to data acquiring conditions, set in the imaging condition setting part 40, for acquiring MR signals multiple times following one excitation while reference MR signals for a phase correction of real space data for imaging, generated based on the MR signals for imaging, can be acquired with setting a PE amount to zero.

Furthermore, the imaging condition setting part 40 can set data acquiring conditions which acquire MR signals using plural coil elements 24c. An imaging method for acquiring MR signals using plural coil elements 24c is called PI (parallel imaging). In many cases, a scan by the EPI method or the FSE method which continuously acquires MR signals is performed by the PI. When the PI is performed, information necessary for the PI, such as the number of the coil element 24c used for acquiring MR signals and information relating each of the coil elements 24c with an imaging part, is set as imaging conditions.

The data processing part 41 has a function to obtain MR signals, acquired by an imaging scan under the imaging conditions set in the imaging condition setting part 40, from the sequence controller 31 to arrange the obtained MR signals in a k-space formed in the k-space data storage part 42; a function to take k-space data from the k-space data storage part 42 to reconstruct image data by image reconstruction processing including an FT (Fourier transform); a function to write image data, obtained by the reconstruction, in the image data storage part 43; and a function to apply necessary image processing of image data taken from the image data storage part 43 to display the image data on the display 34.

When MR signals have been acquired by the PI, unfolding processing of image data corresponding to each of the coil elements 24c is performed based on PI conditions, as post-processing in the PI. Then, unfolded image data are generated by the unfolding processing. The unfolding processing uses a sensitivity distribution of each of the coil elements 24c.

The phase correction part 41A of the data processing part 41 has functions to calculate phase errors of real space data for reference generated based on reference MR data which are MR signals for reference, and to perform a phase correction of real space data for imaging, using a phase correction amount obtained based on the calculated phase errors. In particular, the phase correction part 41A has a function to limit a region for calculating the phase errors of the real space data for reference to a real space region determined based on imaging conditions.

Hereinafter, description will be made with referring to real space data for reference, generated by a 1DFT in the RO direction of reference MR data, as reference real space data. Furthermore, description will be made with referring to a general term for the reference MR data and the reference real space data as reference data.

Figure 8:
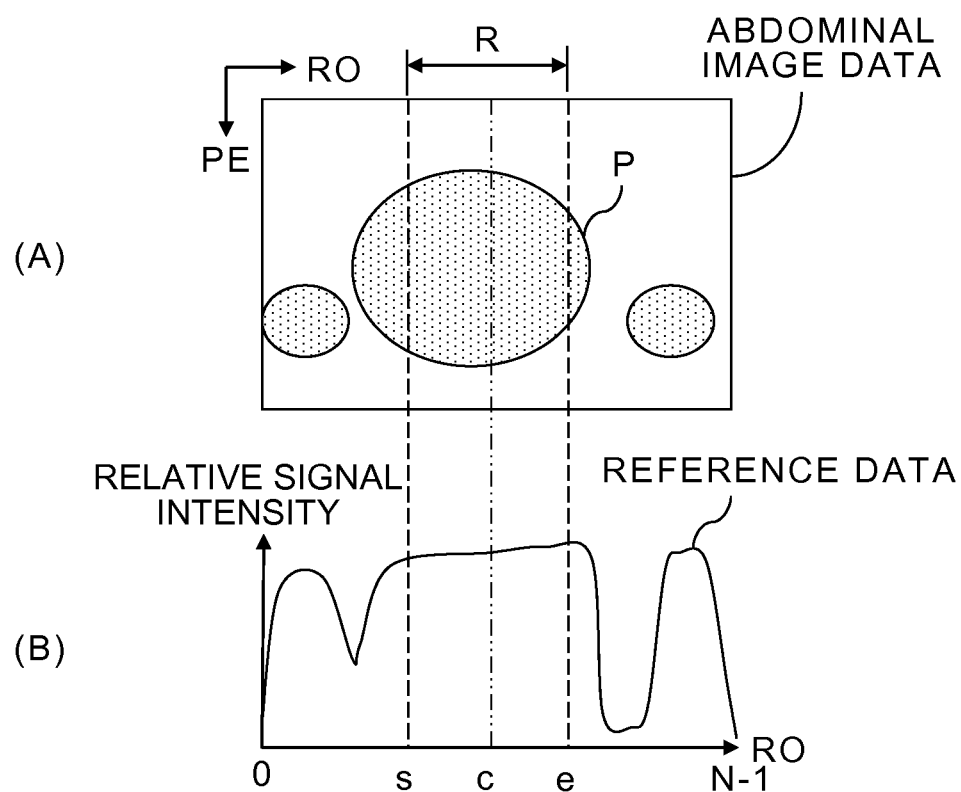
FIG. 8 shows the first method of determining a region for calculating phase errors in the phase correction part shown in FIG. 5.

FIG. 8 shows the first method of determining a region for calculating phase errors in the phase correction part 41A shown in FIG. 5.

(A) of FIG. 8 shows an example of image data which are a target of a phase correction. In (A) of FIG. 8, the horizontal direction shows the RO direction, and the vertical direction shows the PE direction. Meanwhile, (B) of FIG. 8 shows a profile of signal intensities of reference real space data at N sampling points, obtained by a 1DFT of reference MR data. That is, in (B) of FIG. 8, the horizontal axis shows the RO direction, and the vertical axis shows relative signal intensities of the reference real space data.

When an imaging part is the abdomen and an FOV (field of view) in the RO direction is wide, the arms are depicted in the image data, as shown in (A) of FIG. 8. A distribution of phase errors differs between a region of the abdomen and a region of each arm. Furthermore, a non-negligible difference in the distribution of the phase errors also arises between the center of a static magnetic field and a position away from the center of the static magnetic field, according to the distance therebetween. That is, the distribution of the phase errors may show different tendencies according to sampling positions of MR signals in the RO direction.

Therefore, when phase errors are obtained for all regions in the RO direction in the FOV, an inappropriate phase correction amount is calculated. When a phase correction is performed using such an inappropriate phase correction amount, an artifact, such as a ghost, may arise in MR image data.

Thus, phase errors can be calculated with limiting a range in the RO direction in the FOV to a range determined based on a range for acquiring reference real space data, as shown in (A) of FIG. 8. As a method of determining a range for calculating phase errors, a method of setting the range for calculating the phase errors to a predetermined range R, from the start position s to the end position e, whose center c is the center position of the range for acquiring the reference real space data, i.e., the center position of the FOV which is an imaging region can simplify processing.

The predetermined range R to be the range for calculating the phase errors can be previously set empirically to an appropriate width, for example, 20 cm or the like. Alternatively, the predetermined range R may be determined theoretically by a simulation or the like based on design values. Furthermore, a user may be allowed to manually designate or adjust the predetermined range R.

As another method, the predetermined range R, from the start position s to the end position e, whose center c is the position nearest to the center of a magnetic field, in a range for acquiring reference real space data, i.e., in a range in the RO direction in an FOV may be set to a range for calculating phase errors. In this case, coordinate conversion between an object coordinate system fixed to the object P and an apparatus coordinate system fixed to an imaging area can calculate a position C nearest to the center of a magnetic field in the object coordinate system. When the center of the magnetic field lies in the FOV, the predetermined range R, from the start position s to the end position e, whose center c is the center of the magnetic field becomes the range for calculating the phase errors.

Thus, a range for calculating phase errors can be limited based on an FOV, which is one of conditions for acquiring MR signals for imaging, or a range for acquiring reference real space data, which is one of conditions for acquiring reference MR data. Thereby, it becomes possible to selectively obtain only appropriate phase errors in the FOV or the vicinity of the center of a magnetic field even in case that a distribution of phase errors in the abdomen near the center of the magnetic field differs from a distribution of phase errors in each off-center arm part away from the center of the magnetic field.

A specific calculation of phase errors, a calculation of a phase correction amount based on the phase errors, and phase correction processing can be performed by known and arbitrary methods. As an example, a calculation of phase errors, a calculation of a phase correction amount based on the phase errors, and phase correction processing can be performed according to the following calculation in which the start position s and the end position e are parameters.

$$\theta_{1,k} = \arg\left(\sum_{n=s}^{e}(P_k(n)\overline{P_k}(n-1))\right) \ldots 0 \leq k < M \quad (1\text{-}1)$$

$$\theta_{0,k} = \arg\left(\sum_{n=s}^{e}\left(P_k(n)e^{+i(\theta_{1,k}(n-\frac{N}{n}))}\right)\right) \ldots 0 \leq k < M \quad (1\text{-}2)$$

$$\phi_k(x) = e^{-i(\theta_{0,k}+\theta_{1,k}(x-\frac{N}{n}))} \ldots 0 \leq k < M, \quad (1\text{-}3)$$
$$0 \leq x < N$$

$$I'_k(x) = I_k(x)\overline{\phi_k}(x) \ldots 0 \leq k < M, \quad (1\text{-}4)$$
$$0 \leq x < N$$

wherein

N: the sampling number of reference MR data and reference real space data,

M: the number of MR echo signals in the RO direction, $0 \leq k < M$, $0 \leq x < N$, $P_k(x)$: reference real space data corresponding to the k-th echo, $\theta_{1,k}$: the first-order phase error corresponding to the k-th echo, $\theta_{0,k}$: the zero-order phase error corresponding to the k-th echo, $\phi_k(x)$: a complex phase correction amount corresponding to the k-th echo, $I_k(x)$: real space data obtained by 1D-FT of MR signal for imaging corresponding to the k-th echo, and $I_k'(x)$: real space data, after a phase correction, for imaging corresponding to k-th echo.

Expression (1-1) is a calculating expression of the first-order inclining phase errors, expression (1-2) is a calculating expression of the zero-order phase errors having an offset, expression (1-3) is a calculating expression of a phase correction amount, and expression (1-4) is a calculating expression of the phase correction processing. A pixel position corresponding to the start position s of the range R and a pixel position corresponding to the end position e can be obtained by converting the range R cm into a range in units of pixels. The reference real space data are complex data obtained by an LPF (low pass filter) of the reference MR data, and a subsequent 1DFT of the filtered reference MR data.

Another specific method of a calculation of phase errors, a calculation of a phase correction amount based on the phase errors, and phase correction processing is also described in Japanese Patent Application Publication No. H09-253069, for example, besides the above-mentioned calculating method. Note that, when a range for calculating phase errors is not limited to the range R from the start position s to the end position e, expression (2-1) is a calculating expression of the first-order phase errors and expression (2-2) is a calculating expression of the zero-order phase errors.

$$\theta_{1,k} = \arg\left(\sum_{n=1}^{N-1}(P_k(n)\overline{P_k}(n-1))\right) \ldots 0 \leq k < M \quad (2\text{-}1)$$

-continued $$\theta_{0,k} = \arg\left(\sum_{n=0}^{N-1}\left(P_k(n)e^{+i(\theta_{1,k}(n-\frac{N}{n}))}\right)\right) \ldots 0 \leq k < M \quad (2\text{-}2)$$

Figure 9:
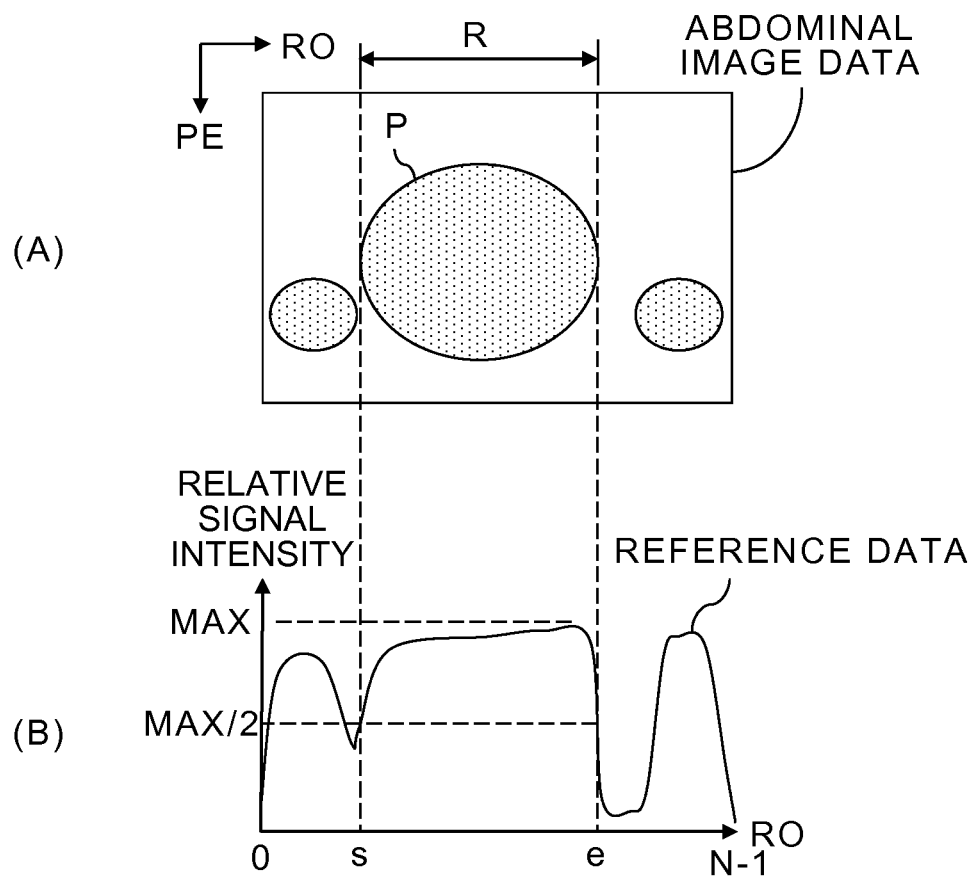
FIG. 9 shows the second method of determining a region for calculating phase errors in the phase correction part shown in FIG. 5.

FIG. 9 shows the second method of determining a region for calculating phase errors in the phase correction part 41A shown in FIG. 5.

(A) of FIG. 9 shows another example of image data which are a target of a phase correction. In (A) of FIG. 9, the horizontal direction shows the RO direction, and the vertical direction shows the PE direction. Meanwhile, (B) of FIG. 9 shows a profile of signal intensities of reference real space data at N sampling points. That is, in (B) of FIG. 9, the horizontal axis shows the RO direction, and the vertical axis shows relative signal intensities of the reference real space data.

As described with referring to (A) of FIG. 8, when an imaging part is the abdomen and an FOV is wide in the RO direction, the arms are depicted in the image data, as shown in (A) of FIG. 9. Thus, the calculation range R of phase errors can be limited based on the signal intensity profile of the reference real space data. For example, a half width of the profile of the reference real space data can be set to the calculation range R of the phase errors, from the start position s to the end position e. Thereby, the phase errors can be obtained using the reference real space data in a range from which the arms have been excluded.

A specific calculation of phase errors, a specific calculation of phase correction amounts based on the phase errors, and specific phase correction processing can be performed by known and arbitrary methods. For example, a calculation of phase errors, a calculation of phase correction amounts based on the phase errors, and phase correction processing can be performed according to the above-mentioned expression (1-1), expression (1-2), expression (1-3) and expression (1-4).

Note that, a profile on a slice plane for locating, sliced from sensitivity map data of the coil elements 24c needed for the PI may also be used instead of the signal intensity profile of the reference real space data. In this case, a half width can also be set to the calculation range R of the phase errors, from the start position s to the end position e.

Figure 10:
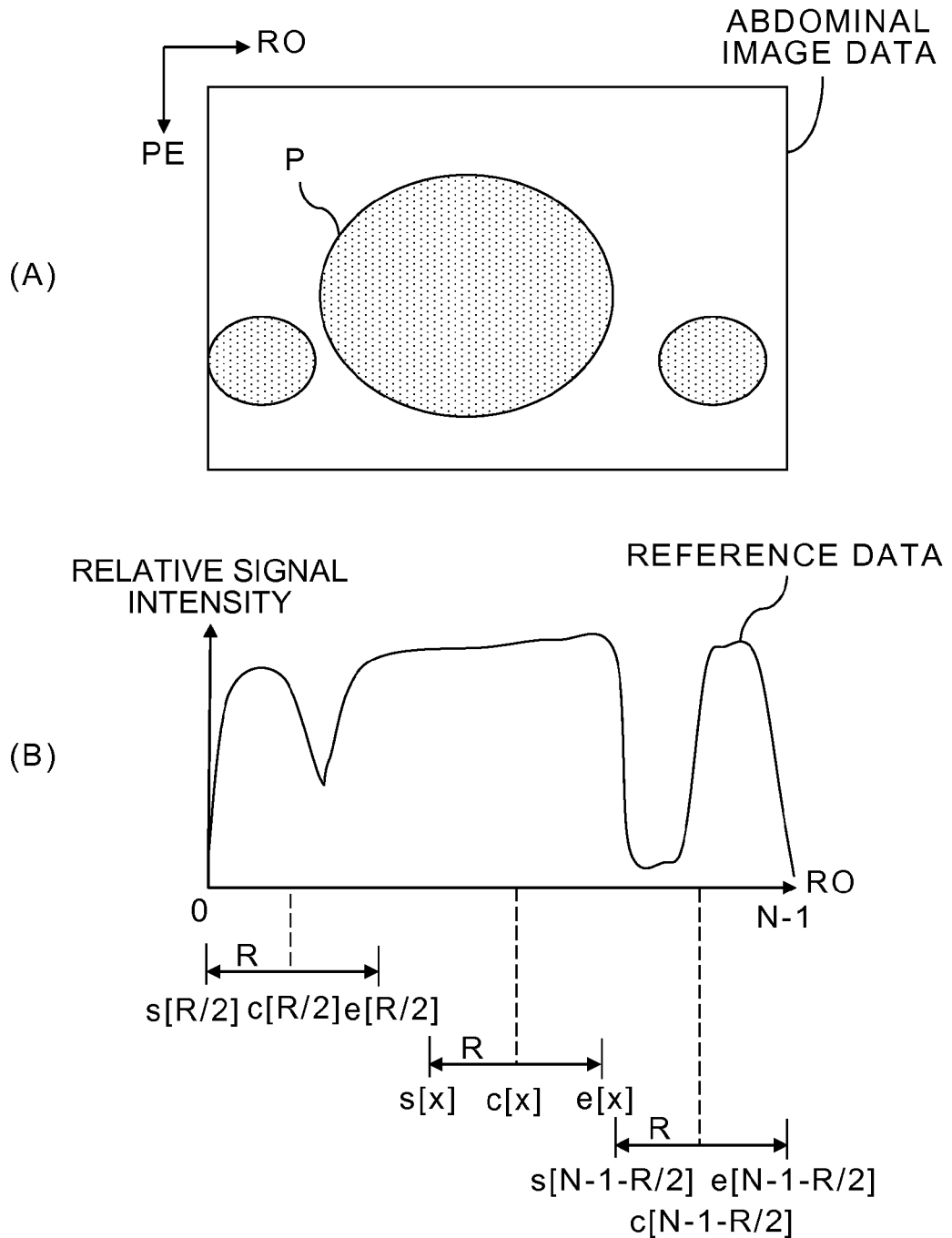
FIG. 10 shows the third method of determining a region for calculating phase errors in the phase correction part shown in FIG. 5.

FIG. 10 shows the third method of determining a region for calculating phase errors in the phase correction part 41A shown in FIG. 5.

(A) of FIG. 10 shows another example of image data which are a target of a phase correction. In (A) of FIG. 10, the horizontal direction shows the RO direction, and the vertical direction shows the PE direction. Meanwhile, (B) of FIG. 10 shows a profile of signal intensities of reference real space data at N sampling points. That is, in (B) of FIG. 10, the horizontal axis shows the RO direction, and the vertical axis shows relative signal intensities of the reference real space data.

As described with referring to (A) of FIG. 8, when an imaging part is the abdomen and an FOV is wide in the RO direction, the arms are depicted in the image data, as shown in (A) of FIG. 10. Thus, as shown in (B) of FIG. 10, the ranges R centering on the positions c[x] designated as correction positions respectively can be set to the calculation ranges R of phase errors. The range R can be determined as 10 cm or the like similarly to the example shown in FIG. 8.

In this case, phase correction processing is not a low-order correction but a high-order correction not less than the second-order correction. Specifically, the zero-order phase error $\theta_{0,k}$ is firstly calculated by the above-mentioned expression (2-2). The calculated zero-order phase error $\theta_{0,k}$ is set to be the zero-order phase correction amount at the center position c[N/2] of the reference real space data. Next, each of the ranges R [cm] of which centers are designated as the correction positions c[x] is converted into pixel units. Thereby, pixel positions of the start position s[x] and the end position e[x] can be obtained.

Then, the first-order phase error $\theta_{1,k}$[N/2] at the center position c[N/2] of the reference real space data can be calculated by expression (3) using reference real space data in a pixel range from the start position s[x] to the end position e[x].

$$\theta_{1,k}[x] = \arg\left(\sum_{n=s[x]}^{e[x]} (P_k(n)\overline{P_k}(n-1))\right) \ldots 0 \le k < M \quad (3)$$

Next, the first-order phase error $\theta_{1,k}$[N/2+1] at the correction position c[N/2+1] adjacent in the positive direction, i.e., on the right of the center position c[N/2] of the reference real space data, is added to the first-order phase error $\theta_{1,k}$[N/2] at the correction position c[N/2] adjacent in the negative direction, i.e., on the left of the correction position c[N/2+1]. Then, an addition result is set to a phase error at the correction position c[N/2]. When the above-mentioned operations are sequentially performed toward the positive direction, then conversely, the operations are sequentially performed toward the negative direction from the center position c[N/2] of the reference real space data, the phase correction amount $\phi_k(x)$ can be obtained as shown in expression (4).

$$\phi_k(x) = \begin{cases} e^{-i\left(\theta_{0,k} + \sum_{n=x}^{N/2-1} \theta_{1,k}[n]\right)} & \ldots 0 \le k < M, \quad 0 \le x < N/2 \\ e^{-i(\theta_{0,k})} & \ldots 0 \le k < M, \quad x = N/2 \\ e^{-i\left(\theta_{0,k} + \sum_{n=N/2+1}^{x} \theta_{1,k}[n]\right)} & \ldots 0 \le k < M, \quad N/2 < x < N \end{cases} \quad (4)$$

Figure 11:
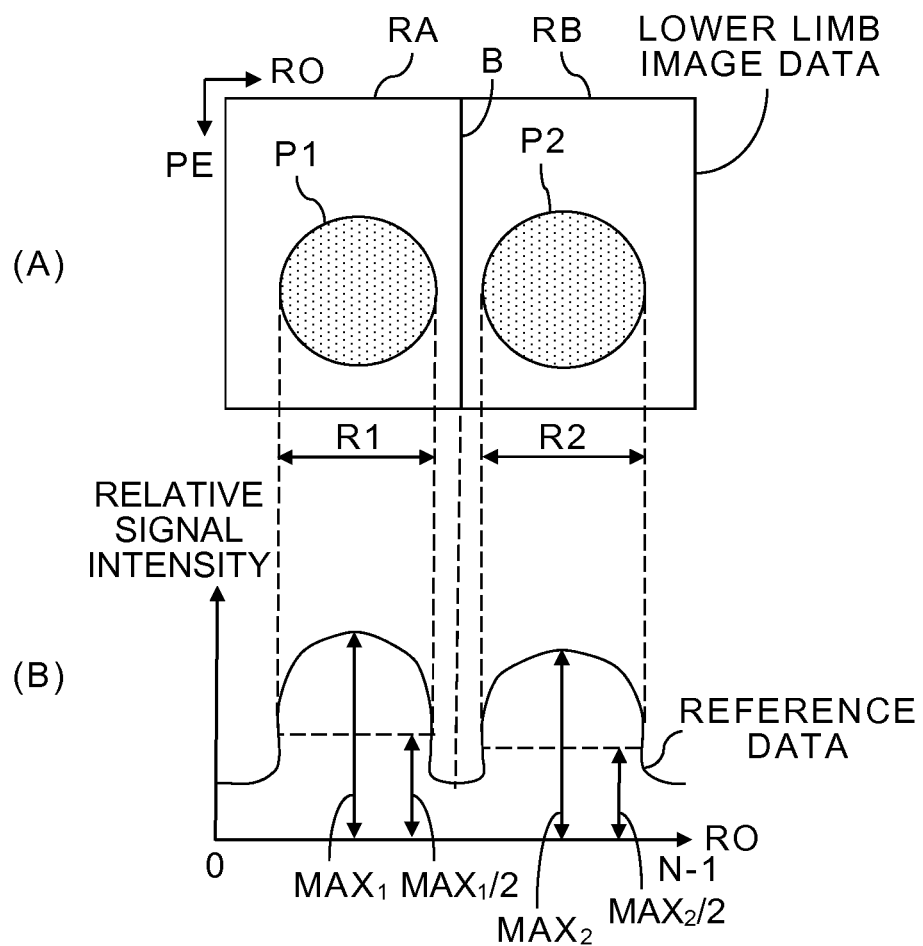
FIG. 11 shows the fourth method of determining a region for calculating phase errors in the phase correction part shown in FIG. 5.

FIG. 11 shows the fourth method of determining a region for calculating phase errors in the phase correction part 41A shown in FIG. 5.

(A) of FIG. 11 shows another example of image data which are a target of a phase correction. In (A) of FIG. 11, the horizontal direction shows the RO direction, and the vertical direction shows the PE direction. When an imaging part is the lower limbs and a distance between the both legs in the RO direction is long, the two parts of interest P1 and P2 lie separately in the RO direction, as shown in (A) of FIG. 11.

In this case, since the two parts of interest P1 and P2 are away from the center of a magnetic field in the RO direction, their distributions of phase errors differ. Thus, a region in which phase correction processing is performed can be divided into two phase correction regions adjacent in the RO direction, i.e., the first phase correction region RA and the second phase correction region RB. Then, obtaining phase errors and subsequent phase correction processing can be performed in each of the first and second calculation ranges R1 and R2 of phase errors, limited in the first and second phase correction regions RA and RB respectively. That is, phase correction processing in the first phase correction region RA can be performed based on the first phase errors obtained in the first calculation range R1 of phase errors, limited in the first phase correction region RA. Similarly, phase correction processing in the second phase correction region RB can be performed based on the second phase errors obtained in the second calculation range R2 of phase errors, limited in the second phase correction region RB.

Note that, the boundary position B between the first phase correction region RA and the second phase correction region RB can be determined by an arbitrary method. For example, the center between two half width regions of signal profiles of reference real space data, the center of a region for acquiring the reference real space data, the center of an FOV or the like can be set as the boundary position B between the first phase correction region RA and the second phase correction region RB. Alternatively, the boundary may be determined using a profile on a slice plane for locating, sliced from sensitivity map data of the coil elements 24c. That is, the boundary position B can be determined by a variety of methods, similar to those in the case where an imaging part is the abdomen.

Furthermore, the first calculation range R1 of phase errors and the second calculation range R2 of phase errors can also be limited to regions, in which the parts of interest P1 and P2 exist, by a variety of methods similar to those in the case where an imaging part is the abdomen. That is, respective calculation regions of phase errors can be determined using a signal profile of reference real space data or a profile on a slice plane for locating, sliced from sensitivity map data of the coil elements 24c.

Note that, in the example shown in FIG. 11, the center between the half widths of the two local maximum values $MAX_1$ and $MAX_2$ of the reference real space data has been set to the boundary position B between the first phase correction region RA and the second phase correction region RB. Then, the half width of the reference real space data in the first phase correction region RA has been set to the first calculation range R1 of phase errors while the half width of the reference real space data in the second phase correction region RB has been set to the second calculation range R2 of phase errors.

Figure 12:
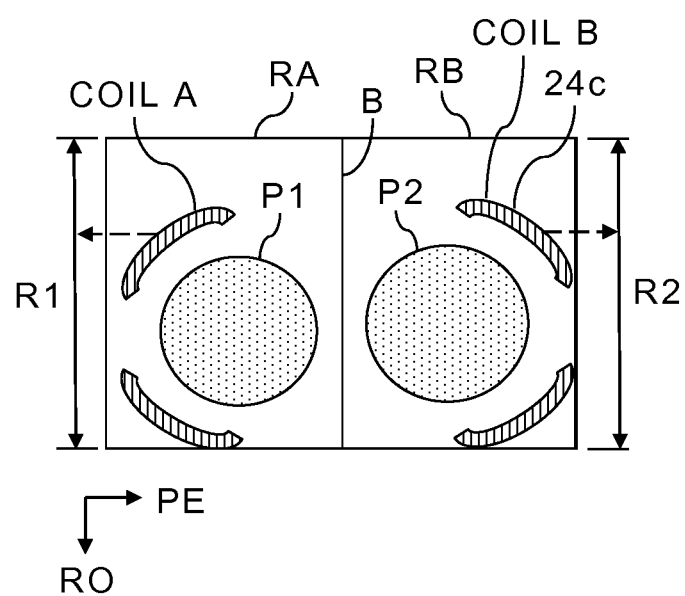
FIG. 12 shows the fifth method of determining a region for calculating phase errors in the phase correction part shown in FIG. 5.

FIG. 12 shows the fifth method of determining a region for calculating phase errors in the phase correction part 41A shown in FIG. 5.

FIG. 12 shows another example of image data which are a target of a phase correction. In FIG. 12, the horizontal direction shows the PE direction, and the vertical direction shows the RO direction. When an imaging part is the lower limbs and a distance between the both legs in the PE direction is long, the two parts of interest P1 and P2 exist separately in the PE direction, as shown in FIG. 12.

In this case, since the two parts of interest P1 and P2 are away from the center of a magnetic field in the PE direction, their distributions of phase errors differ. Thus, a region in which phase correction processing is performed can be divided into two phase correction regions adjacent in the PE direction, i.e., the first phase correction region RA and the second phase correction region RB. The boundary position B between the first phase correction region RA and the second phase correction region RB can be determined by a method similar to that in the example shown in FIG. 11.

When reference MR data are acquired using plural coil elements 24c, the coil elements 24c are usually arranged near the parts of interest P1 and P2, as shown in FIG. 12. Thus, phase errors in the first and second phase correction regions RA and RB can be calculated using reference real space data sets acquired using the coil elements 24c nearest to the parts of interest P1 and P2 respectively.

In the example shown in FIG. 12, phase errors in the first phase correction region RA are calculated based on reference real space data acquired by the COIL A which has acquired reference MR data with the largest signal intensities. Then, phase correction processing in the first phase correction region RA is performed based on the calculated phase errors. Similarly, phase errors in the second phase correction region RB are calculated based on reference real space data acquired by the COIL B which has acquired reference MR data with the largest signal intensities. Then, phase correction processing in the second phase correction region RB is performed based on the calculated phase errors.

That is, the region for calculating phase errors can be limited in the PE direction by dividing the region, in which phase correction processing is performed, into two phase correction regions adjacent in the PE direction, i.e., the first and second phase correction regions RA and RB, without limiting the calculation regions R1 and R2 of phase errors in the RO direction.

As described above, phase errors of reference real space data can be calculated in a limited real space region, in order to avoid calculating inappropriate phase errors due to non-uniformity in a magnetic field or the like. Then, the real space region, which is a target of calculating the phase errors, can be determined based on conditions for acquiring reference MR data or conditions of the reference real space data or the like, corresponding to the conditions for acquiring the reference MR data, as described above.

For example, at least one real space region which is a target for calculating phase errors can be set based on a region for acquiring reference real space data. As a specific example, a region within the designated range R centering on the center of the region for acquiring the reference real space data can be set as a real space region which is a target for calculating phase errors, as shown in FIG. 8. Alternatively, a region within a designated range R centering on the position, nearest to the center of a magnetic field, in the region for acquiring the reference real space data can be set as a real space region which is a target for calculating phase errors.

Alternatively, a real space region which is a target for calculating the phase errors can also be set based on a part of interest or parts of interest included in the region for acquiring the reference real space data. As a specific example, a real space region which is a target for calculating the phase errors or real space regions for calculating the phase errors can be set based on a signal intensity profile of the reference real space data, as shown in FIG. 9 and FIG. 11. Alternatively, a real space region which is a target for calculating the phase errors can also be set based on a profile of sensitivity map data of at least one RF coil 24. In this case, a part of interest or parts of interest, such as the abdominal region or the lower limb regions, of the object P can be specified based on a half width of amplitudes of a profile or the like.

Furthermore, as another example, regions within designated ranges R centering on phase correction positions respectively, in the region for acquiring the reference real space data, can be set as real space regions which are targets for calculating the phase errors, as shown in FIG. 10.

When lower limbs are parts of interest included in the region for acquiring the reference real space data, and the right and left direction of the object P is the RO direction, the first phase errors in the first real space region R1 and the second phase errors in the second real space region R2 can be calculated, as shown in FIG. 11. Subsequently, the phase correction based on the first phase errors can be performed in the region RA including the first real space region R1 while the phase correction based on the second phase errors can be performed in the region RB including the second real space region R2. In this case, the boundary B between the region RA including the first real space region R1 and the region RB including the second real space region R2 can be determined based on a signal intensity profile of the reference real space data or a profile of sensitivity map data of at least one RF coil 24.

Meanwhile, when lower limbs are parts of interest included in the region for acquiring the reference real space data, and the right and left direction of the object P is the PE direction, the first phase errors in the first real space region RA and the second phase errors in the second real space region RB can be calculated, as shown in FIG. 12. Subsequently, the phase correction based on the first phase errors can be performed in the first real space region RA while the phase correction based on the second phase errors can be performed in the second real space region RB. In this case, the first phase errors and the second phase errors can be respectively calculated based on the reference MR data sets with the largest intensities acquired by coil elements 24c (COIL A, COIL B), which have acquired the reference MR data with the largest intensities in the first real space region RA and the second real space region RB respectively, out of the coil elements 24c used for acquiring the reference MR data.

Note that, in case of setting a real space region for calculating phase errors with limitation in the RO direction of reference MR data, a range narrower than an imaging region is set as the real space region. Furthermore, in case of setting a real space region for calculating phase errors based on a part of interest or parts of interest, a region or regions according to an imaging protocol related to the part of interest or the parts of interest can be set as the real space region for calculating the phase errors.

The method of determining a real space region for calculating phase errors, as described above, can be selected from plural determination methods which have previously been prepared to be selectable. That is, a real space region which is a target of calculating phase errors can be determined by a determination method selected from determination methods of the real space region. Furthermore, a method of determining the real space region, which has been selected once can also be altered into another determination method. Conversely, a method of determining the real space region can also be selected automatically according to arbitrary conditions, such as a protocol used for imaging.

As a matter of course, a choice which does not limit a real space region for calculating phase errors may also be prepared. That is, it can be determined whether to perform phase correction processing with limiting a real space region which is a target for calculating phase errors, by operating the input circuit 33.

On the other hand, the image reconstruction part 41B of the data processing part 41 has a function to generate real space data by applying an FT to k-space data. Thus, MR image data can be generated based on MR signals for imaging with a phase correction of real space data for imaging based on phase errors, by data processing in the image reconstruction part 41B and the phase correction part 41A.

Next, an operation and action of the magnetic resonance imaging apparatus 20 will be described.

Figure 13:
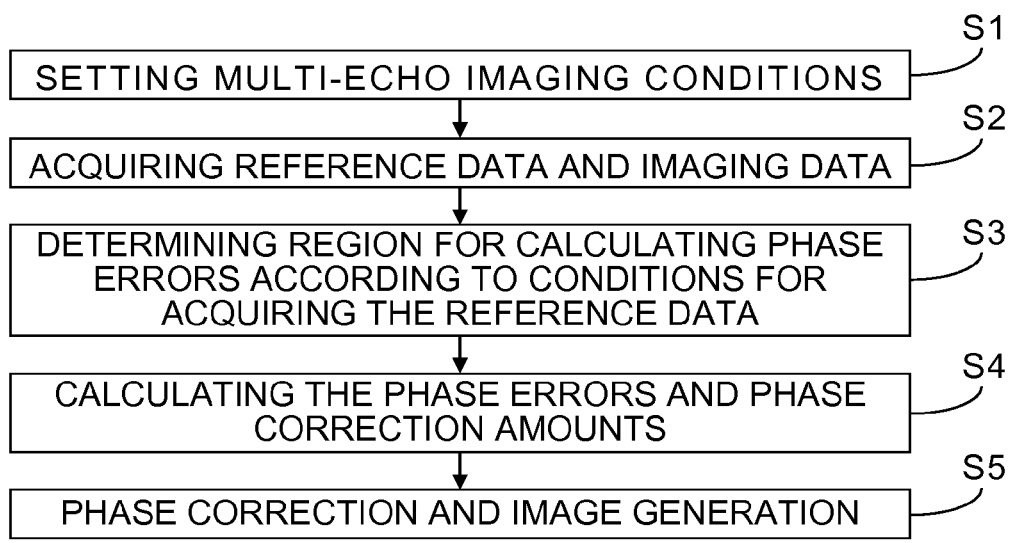
FIG. 13 is a flow chart showing an operation and processing of the magnetic resonance imaging apparatus shown in FIG. 1.

FIG. 13 is a flow chart showing an operation and processing of the magnetic resonance imaging apparatus 20 shown in FIG. 1.

Firstly, an object P is set on the bed 37, and a static magnetic field is generated in an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated in the imaging area.

Then, in step S1, data acquiring conditions which acquire MR signals multiple times following one excitation are set as imaging conditions for an MR multi-echo data acquisition. That is, a high speed imaging sequence, such as an FSE sequence as shown in FIG. 6 or an EPI sequence as shown in FIG. 7, is set in the imaging condition setting part 40. In addition, a pulse sequence which does not apply PE gradient magnetic field pulses is set as acquiring conditions for reference MR data for a phase correction of real space data for imaging, generated based on MR signals for imaging.

Next, in step S2, reference MR data and imaging data are acquired according to the imaging conditions set in the imaging condition setting part 40. Specifically, elements, such as the sequence controller 31 and the static field magnet 21, of the magnetic resonance imaging apparatus 20 for performing a data acquisition acquire MR signals for imaging according to the set data acquiring conditions and acquire reference MR data with setting a PE amount to zero.

A more specific flow of a data acquisition is as follows.

The input circuit 33 sends instruction of starting a scan to the imaging condition setting part 40. Then, the imaging condition setting part 40 outputs the imaging conditions including a pulse sequence to the sequence controller 31. The sequence controller 31 drives the gradient power supply 27, the transmitter 29, and the receiver 30 in accordance with the pulse sequence, thereby generating a gradient magnetic field at the imaging area having the set object P, and further generating RF signals from the RF coil 24.

Consequently, the RF coil 24 receives MR signals generated due to the nuclear magnetic resonance in the object P. Then, the receiver 30 receives the MR signals from the RF coil 24 and generates raw data, which are the digitalized MR signals, by A/D (analog to digital) conversion subsequently to predetermined signal processing of the MR signals. The receiver 30 supplies the generated raw data to the sequence controller 31. The sequence controller 31 supplies the raw data to the computer 32. The data processing part 41 of the computer 32 arranges the raw data as k-space data to the k-space formed in the k-space data storage part 42.

Next, in step S3, a region for calculating phase errors is determined according to conditions for acquiring reference MR data or conditions corresponding to the conditions for acquiring the reference MR data. Specifically, the phase correction part 41A of the data processing part 41 determines the region for calculating phase errors by a determination method as exemplified from FIG. 8 to FIG. 12 or another designated determination method. Thereby, the appropriate region for calculating phase errors according to a part of interest or parts of interest is determined.

Next, in step S4, phase errors and phase correction amounts are calculated by the phase correction part 41A. Specifically, the phase errors of the reference real space data in the real space region determined based on the conditions for acquiring the reference MR data or the conditions corresponding to the conditions for acquiring the reference MR data are calculated. Subsequently, the phase correction amounts are calculated based on the phase errors.

Next, in step S5, phase correction processing based on the calculated phase correction amounts and image generation processing are performed. Specifically, MR image data are generated based on MR signals for imaging with a phase correction of the real space data for imaging based on the phase errors, by data processing in the image reconstruction part 41B and the phase correction part 41A.

Note that, a method of determining a region for calculating the phase errors can be selected from plural determination methods. The method of determining the region for calculating the phase errors can be selected at the time of setting the imaging conditions or immediately before the phase correction processing.

Figure 14:
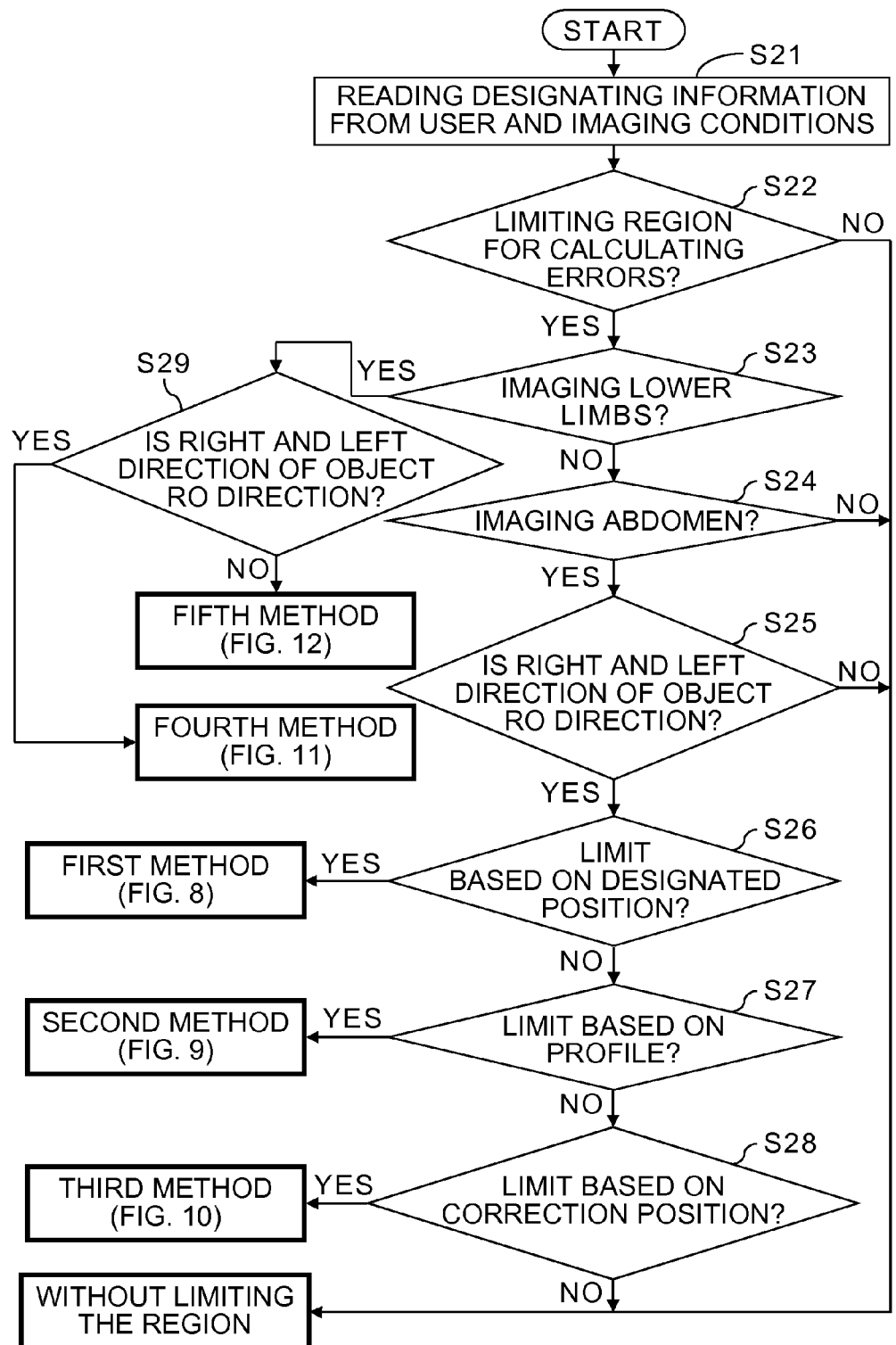
FIG. 14 is a flow chart showing an example of selection methods in case of selecting a method of determining a region for calculating phase errors.

FIG. 14 is a flow chart showing an example of selection methods in case of selecting a method of determining a region for calculating phase errors.

As shown in FIG. 14, in step S21, designating information from a user and imaging conditions, which are necessary for determination for selecting a method of determining a region for calculating phase errors, are read into the phase correction part 41A. Examples of the designating information from a user include information for designating whether to limit a region for calculating phase errors or necessary conditions, such as parameters, for phase correction processing in case of limiting the region for calculating the phase errors.

Meanwhile, examples of the imaging conditions read into the phase correction part 41A include conditions, used for the determination, belonging to phase correction processing conditions, out of an imaging part, an imaging protocol related to an imaging part, a region for acquiring reference MR data and reference real space data, and an imaging region.

Then, a method of determining a region for calculating phase errors can be selected by the determination processing from step S22 to step S28.

In step S22, it is determined whether to limit a region for calculating phase errors. Therefore, when direction information for limiting the region for calculating the phase errors is not input from the input circuit 33 to the phase correction part 41A, calculating the phase errors without limiting the region for calculating the phase errors is a phase correction processing condition.

Meanwhile, when the direction information for limiting the region for calculating the phase errors has been input from the input circuit 33 to the phase correction part 41A, the determination of step S23 is performed. In step S23, it is determined whether an imaging part is the lower limbs. Information necessary for determining whether the imaging part is the lower limbs can be obtained, by the phase correction part 41A, as designating information from a user for specifying the imaging part or imaging conditions, such as the imaging part or an imaging protocol related with the imaging part.

When the imaging part is determined not to be the lower limbs, it is determined whether the imaging part is the abdomen in step S24. The determination of whether the imaging part is the abdomen can be performed similarly to the determination of whether the imaging part is the lower limbs. When the imaging part is also determined not to be the abdomen, the phase correction processing conditions are to calculate the phase errors without limiting the region for calculating the phase errors.

When the imaging part is determined to be the abdomen, it is determined whether the right and left direction of the object P is the RO direction in step S25. This determination can also be performed based on designating information from a user or the imaging conditions, which have been read. When the right and left direction of the object P is determined not to be the RO direction, the phase correction processing conditions are to calculate the phase errors without limiting the region for calculating the phase errors.

Meanwhile, when the right and left direction of the object P is determined to be the RO direction, a limiting method of the region for calculating the phase errors is determined based on designating information from a user, in step S26 to step S28.

When a predetermined range from a designated position, such as the center of an FOV or a position nearest to the center of a magnetic field in the FOV, is set to be the region for calculating the phase errors, the first method of determining the region for calculating the phase errors, exemplified in FIG. 8, is selected. Meanwhile, when a region or regions corresponding to a part of interest or parts of interests are set to be the region or regions for calculating the phase errors, based on a signal intensity profile of the reference real space data in an FOV or a profile of sensitivity map data of the coil elements 24c, the second method of determining the region for calculating the phase errors, exemplified in FIG. 9, or a similar method, of determining the region for calculating the phase errors, based on the profile of the sensitivity map data of the coil elements 24c, is selected. Furthermore, when predetermined ranges from phase correction positions in an FOV are set to be the regions for calculating the phase errors, the third method of determining the region for calculating the phase errors, exemplified in FIG. 10, is selected.

When the designating information from a user does not correspond to any of the first, second and third determination methods, the phase correction processing conditions are to calculate the phase errors without limiting the region for calculating the phase errors.

When the imaging part is determined to be the lower limbs in step S23, it is determined whether the right and left direction of the object P is the RO direction in step S29. The determination of step S29 is similar to the determination of step S25.

When the right and left direction of the object P is determined to be the RO direction in step S29, the fourth method of determining the region for calculating the phase errors, exemplified in FIG. 11, is selected. Meanwhile, when the right and left direction of the object P is determined not to be the RO direction in step S29, the fifth method of determining the region for calculating the phase errors, exemplified in FIG. 12, is selected.

That is, when the imaging part is the lower limbs, a phase correction region is divided into a region including the right lower limb of the object P and a region including the left lower limb of the object P. Then, phase errors are individually calculated in each of the two divided phase correction regions.

When the right and left direction of the object P is the RO direction, each of the regions for calculating phase errors in the RO direction is further limited to a region corresponding to the part of interest, based on a signal intensity profile of the reference real space data in an FOV, as exemplified in FIG. 11, or a profile of sensitivity map data of the coil elements 24c. Meanwhile, when the right and left direction of the object P is not the RO direction, phase errors are calculated based on reference real space data sets corresponding to the coil elements 24c nearest to the parts of interest respectively.

That is, the magnetic resonance imaging apparatus 20 as described above is configured to limit a region for calculating phase errors necessary for a phase correction performed in imaging with a multi-echo acquisition, based on conditions, such as an FOV, of acquiring reference data or conditions corresponding to the conditions of acquiring the reference data.

Therefore, according to the magnetic resonance imaging apparatus 20, a phase correction based on inappropriate phase errors due to an influence of non-uniformity in a magnetic field or the like can be avoided. Thereby, a higher quality image with reduced fluctuations can be obtained compared with a case where a phase correction is performed based on phase errors calculated from reference data in whole region in the RO direction.

Furthermore, an appropriate real space region for calculating phase errors can be determined according to imaging conditions, such as an FOV or an imaging part. Then, a region for calculating phase errors according to imaging conditions can be determined under conditions designated by a manual operation of a user. On the contrary, when a region for calculating phase errors is limited automatically according to imaging conditions by a previously determined method, a phase correction can be performed based on phase errors calculated from an appropriate calculation region even when a user does not pay special attention to features of an imaging part or a part of interest.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, a region for acquiring reference data can also be limited according to a region for calculating phase errors.

What is claimed is:

1. A magnetic resonance imaging apparatus comprising:
a magnet, a gradient coil and at least one radio frequency coil for acquiring magnetic resonance signals for imaging according to data acquiring conditions for acquiring magnetic resonance signals multiple times following one excitation, and acquiring magnetic resonance signals for reference for a phase correction of real space data for the imaging, the real space data being generated based on the magnetic resonance signals for the imaging; and
processing circuitry configured to
calculate a phase error, in a real space region, of real space data for reference, the real space data for the reference being generated based on the magnetic resonance signals for the reference, the real space region being determined based on conditions of acquiring the magnetic resonance signals for the reference or conditions corresponding to the conditions of acquiring the magnetic resonance signals for the reference, and
generate magnetic resonance image data based on the magnetic resonance signals for the imaging with the phase correction of the real space data for the imaging based on the calculated phase error.

2. A magnetic resonance imaging apparatus of claim 1, wherein the processing circuitry is configured to set the real space region based on a region for acquiring the real space data for the reference.

3. A magnetic resonance imaging apparatus of claim 2, wherein the processing circuitry is configured to set the real space region as a range designated with reference to a center of the region for acquiring the real space data for the reference.

4. A magnetic resonance imaging apparatus of claim 2, wherein the processing circuitry is configured to set the real space region as a range designated with reference to a position in the region for acquiring the real space data for the reference, the position being nearest to a center of a magnetic field.

5. A magnetic resonance imaging apparatus of claim 2, wherein the processing circuitry is configured to set the real space region based on a part of interest included in the region for acquiring the real space data for the reference.

6. A magnetic resonance imaging apparatus of claim 2, wherein the processing circuitry is configured to set the real space region as designated ranges each centering on a phase correction position in the region for acquiring the real space data for the reference.

7. A magnetic resonance imaging apparatus of claim 5, wherein the processing circuitry is configured to set the real space region as a region according to an imaging protocol related to the part of interest.

8. A magnetic resonance imaging apparatus of claim 1, wherein the processing circuitry is configured to set the real space region based on a signal intensity profile of the real space data for the reference.

9. A magnetic resonance imaging apparatus of claim 1, wherein the processing circuitry is configured to set the real space region based on a profile of sensitivity map data of a radio frequency coil.

10. A magnetic resonance imaging apparatus of claim 1, wherein the processing circuitry is configured to
calculate a first phase error in a first real space region and a second phase error in a second real space region,
apply a phase correction, based on the first phase error, to a region including the first real space region, and
apply a phase correction, based on the second phase error, to a region including the second real space region.

11. A magnetic resonance imaging apparatus of claim 10, wherein the processing circuitry is configured to determine a boundary between the region including the first real space region and the region including the second real space region, based on a signal intensity profile of the real space data for the reference or a profile of sensitivity map data of a radio frequency coil.

12. A magnetic resonance imaging apparatus of claim 1, wherein the processing circuitry is configured to
calculate a first phase error in a first real space region and a second phase error in a second real space region,
apply a phase correction, based on the first phase error, to the first real space region, and
apply a phase correction, based on the second phase error, to the second real space region,
the processing circuitry being configured to
calculate the first phase error based on magnetic resonance signals for reference, having largest intensities, acquired in the first real space region by a first coil element out of coil elements used for acquiring the magnetic resonance signals for the reference, and
calculate the second phase error based on magnetic resonance signals for reference, having largest intensities, acquired in the second real space region by a second coil element out of the coil elements.

13. A magnetic resonance imaging apparatus of claim 1, wherein the processing circuitry is configured to set a real space region in a readout direction of the magnetic resonance signals for the reference.

14. A magnetic resonance imaging apparatus of claim 1, wherein the processing circuitry is configured to set the real space region as a range narrower than an imaging region.

15. A magnetic resonance imaging apparatus of claim 1, wherein the processing circuitry is configured to determine the real space region by a determination method selected from plural determination methods of the real space region.

16. A magnetic resonance imaging method comprising:
acquiring magnetic resonance signals for imaging according to data acquiring conditions for acquiring magnetic resonance signals multiple times following one excitation, and acquiring magnetic resonance signals for reference for a phase correction of real space data for the imaging, the real space data being generated based on the magnetic resonance signals for the imaging; and
calculating a phase error, in a real space region, of real space data for reference and generating magnetic resonance image data based on the magnetic resonance signals for the imaging with the phase correction of the real space data for the imaging based on the calculated phase error, the real space data for the reference being generated based on the magnetic resonance signals for the reference, the real space region being determined based on conditions of acquiring the magnetic resonance signals for the reference or conditions corresponding to the conditions of acquiring the magnetic resonance signals for the reference.

* * * * *